(12) United States Patent
Erhardt et al.

(10) Patent No.: US 8,507,549 B2
(45) Date of Patent: Aug. 13, 2013

(54) METHODS FOR SYNTHESIZING GLYCINOLS, GLYCEOLLINS I AND II AND ISOFLAVENES AND CHROMANES USING A WITTIG REACTION, AND COMPOSITIONS MADE THEREWITH

(75) Inventors: Paul W. Erhardt, Sylvania, OH (US); Rahul S. Khupse, Toledo, OH (US); Amarjit Luniwal, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 13/346,059

(22) Filed: Jan. 9, 2012

(65) Prior Publication Data

US 2012/0115942 A1 May 10, 2012

Related U.S. Application Data

(63) Continuation-in-part of application No. 12/921,013, filed as application No. PCT/US2009/035803 on Mar. 3, 2009.

(60) Provisional application No. 61/067,883, filed on Mar. 3, 2008.

(51) Int. Cl.
 *A61K 31/353* (2006.01)
 *C07D 493/04* (2006.01)
 *C07D 493/14* (2006.01)
 *C07D 311/58* (2006.01)

(52) U.S. Cl.
 USPC ............ 514/456; 549/406; 549/383; 549/382

(58) Field of Classification Search
 USPC .......................... 514/456; 549/406, 383, 382
 See application file for complete search history.

(56) References Cited

U.S. PATENT DOCUMENTS

| 2006/0167083 A1* | 7/2006 | Kelly ........................... 514/454 |
|---|---|---|
| 2006/0246162 A1 | 11/2006 | Cleveland et al. |
| 2008/0200537 A1 | 8/2008 | Cleveland et al. |
| 2010/0298581 A1 | 11/2010 | Wang et al. |
| 2010/0298582 A1 | 11/2010 | Wang et al. |
| 2011/0144195 A1 | 6/2011 | Erhardt et al. |
| 2011/0237505 A1 | 9/2011 | Burow et al. |

FOREIGN PATENT DOCUMENTS

| WO | 2006118871 A2 | 11/2006 |
|---|---|---|
| WO | 2009111428 A4 | 9/2009 |
| WO | 2010075418 A2 | 7/2010 |
| WO | 2011087857 A2 | 7/2011 |

OTHER PUBLICATIONS

PCT International Preliminary Report on Patentability, PCT/US2009/035803 filed Mar. 3, 2009, dated Sep. 7, 2010.
Burali, C. et al., "Synthesis and Anti-Rhinovirus Activity of Halogen-Substituted Isoflavenes and Isoflavans," Eur. J. Med., 1987, pp. 119-123, vol. 22.
Evans, L. A. et al.,"Intramolecular Wittig Reactions with Esters Utilising Triphenylphosphine and Dimethyl Acetylenedicarboxylate," Tet Letters, 2002, pp. 299-301, vol. 43.
Khupse, R.S. et al., "Total Synthesis of Racemic, Natural (−) and Unnatural (+) Glyceollin I," Organic Letters, 2008, pp. 5007-5010, vol. 10, No. 21.
Khupse, R.S. et al., "Total Synthesis of Xanthohumol," J. Nat. Prod., 2007, pp. 1507-1509, vol. 70.
Khupse, R.S. et al., "Practival Synthesis of Lespedezol A1," J. Nat. Prod, 2008, pp. 275-277, vol. 71.
Kinder, F.R. et al., "Synthesis of 3-Pyrrolines by an Intramolecular Wittig Reaction," J. Org. Chem., 1991, pp. 6475-6477, vol. 56.
Kumar, P. et al., "A Novel Synthesis of 4H-Chromen-4-ones via Intramolecular Wittig Reaction," Organic Letters, 2000, pp. 3821-3823, vol. 2, No. 24.
Luniwal, A. et al., "Total Synthesis of Racemic and Natural Glycinol," J. Nat. Prod., 2009, pp. 2072-2075, vol. 72.
Luniwal, A. et al., "Total Synthesis of (±)-Vestitol and Bolusanthin III Using a Wittig Strategy," Syntell, 2011, pp. 1605-1607, No. 11.
Yuan, Y. et al., "Total Synthesis of Kendomycin: A Macro-C-Glycosidation Approach," J. Am. Chem. Soc., 2004, pp. 14720-14721, vol. 126.

* cited by examiner

*Primary Examiner* — Kristin Vajda

(74) *Attorney, Agent, or Firm* — MacMillan, Sobanski & Todd, LLC

(57) ABSTRACT

Methods for synthesizing glycinols, glyceollins I and II, and isoflavene and chromane compounds using a Wittig reaction, compositions made therewith, and uses thereof are described.

4 Claims, 4 Drawing Sheets

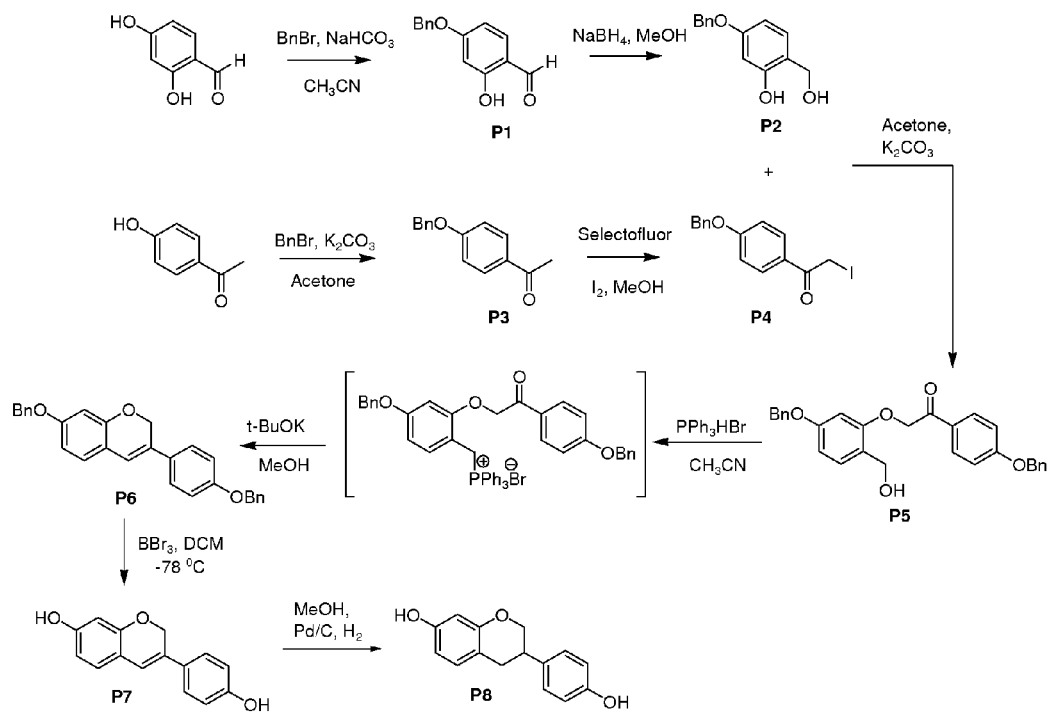
Figure 1 - Scheme 1
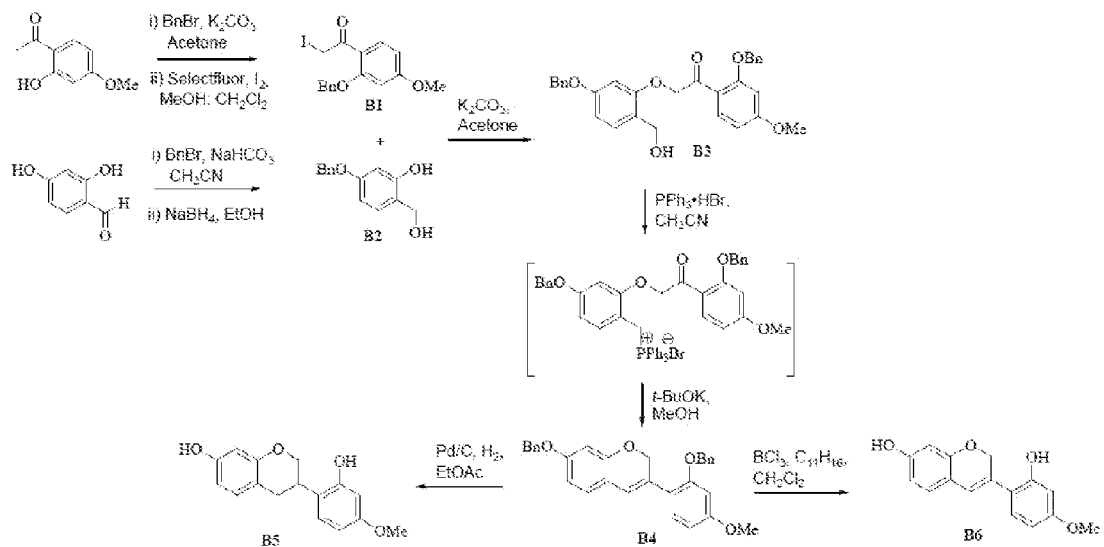
Figure 2 - Scheme 2

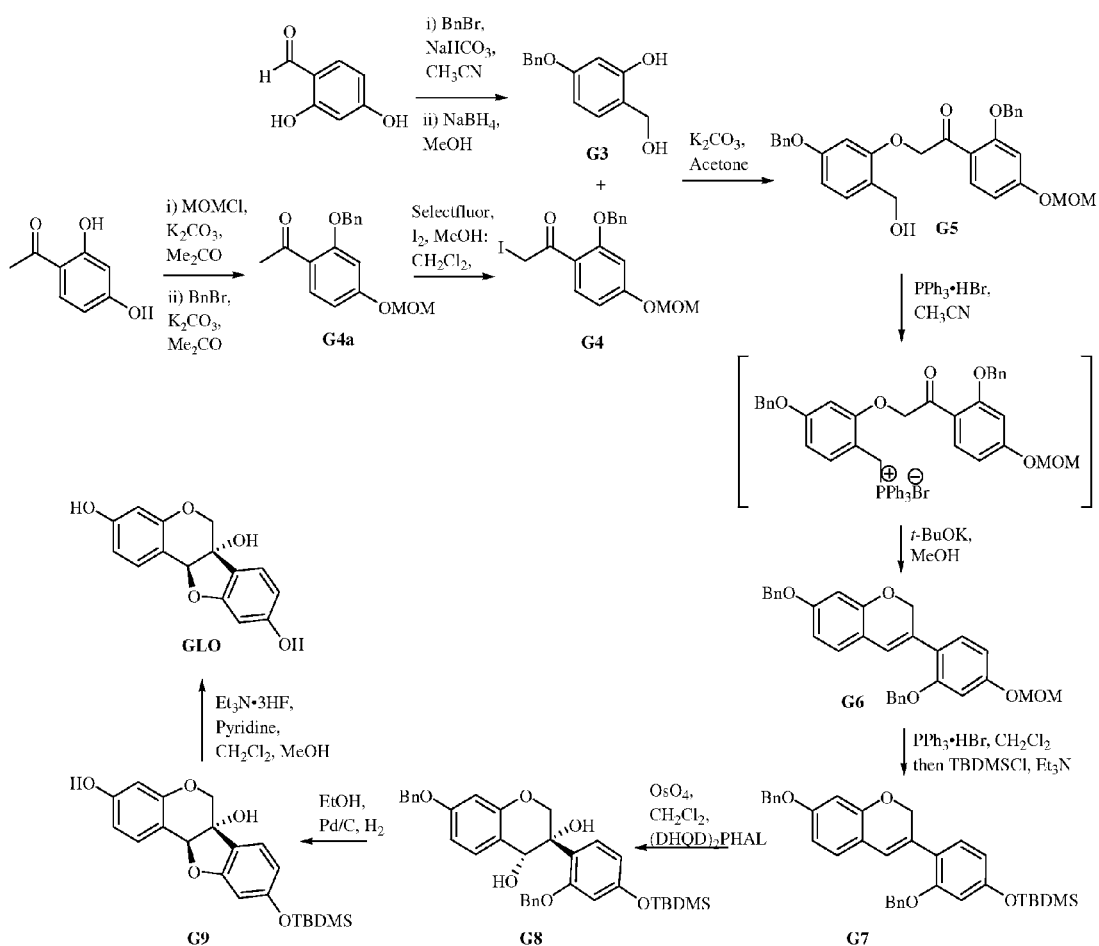
Figure 3 - Scheme 3

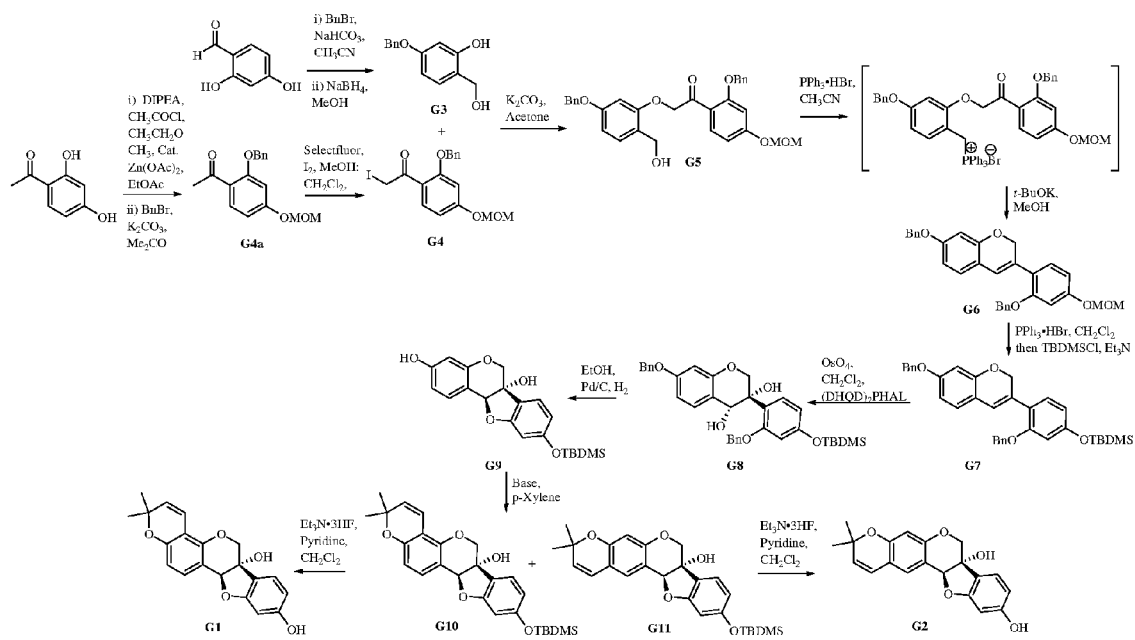
Figure 4 - Scheme 4

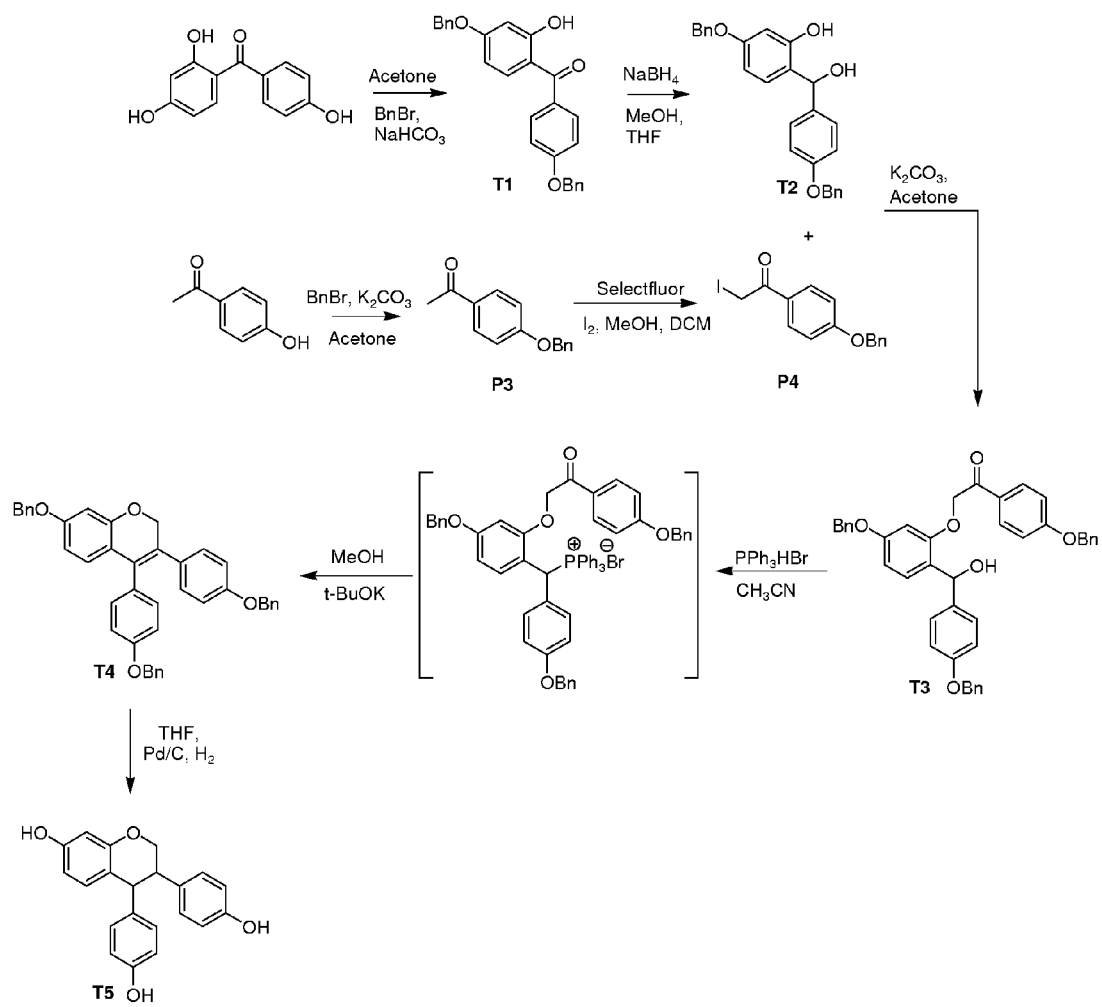
Figure 5 - Scheme 5

METHODS FOR SYNTHESIZING GLYCINOLS, GLYCEOLLINS I AND II AND ISOFLAVENES AND CHROMANES USING A WITTIG REACTION, AND COMPOSITIONS MADE THEREWITH

CROSS-REFERENCE TO RELATED APPLICATIONS

This is a is a continuation-in-part of U.S. Ser. No. 12/921, 013, having a filing date of Dec. 15, 2010 which is national stage application filed under 37 CFR §1.371 of international application PCT/US2009/035083 filed Mar. 3, 2009, which claims the priority to U.S. Provisional Application No. 61/067,883, filed Mar. 3, 2008, the entire disclosures of which are expressly incorporated herein by reference.

STATEMENT REGARDING FEDERALLY SPONSORED RESEARCH

The invention was made with U.S. Government support under grant Number 58-6435-8-323 by the United States Department of Agriculture (USDA ARS SRRC). The United States Government has certain rights in the invention.

TECHNICAL FIELD AND INDUSTRIAL APPLICABILITY OF THE INVENTION

The present invention relates to methods for synthesizing glycinols, glyceollins I and II, and isoflavene and chromane compounds using a Wittig reaction, compositions made therewith, and uses.

BACKGROUND

The glyceollins (GLYs) are natural product compounds that display properties indicative for use as cancer prevention and treatment agents. To date, supplies of the GLYs must be obtained by their induced biosynthesis in soybean plant parts followed by tedious extraction and purification procedures which provide extremely low yields. Thus, there is an immediate need for improved methods to produce various GLY compounds for further development, as well as a longer-term need for producing large supplies of selected GLY members for eventual use within the marketplace.

The WO2009/111428A2 generally describes a method for synthesizing GLYs I and II that can be used to prepare a variety of GLY-related compounds, including glycinol and certain synthetic intermediates that have-novel compositions of matter. The purified, individual GLY members, synthetic intermediates and selected analogs display useful pharmacological properties similar to the naturally-derived materials.

There is still a need, however, for new methods for the production of variously substituted isoflavene natural product analogs.

SUMMARY OF THE INVENTION

In a first aspect, there is provided herein a process for preparing 4',7-dioxygenated-isoflav-3-ene, and chromane compounds, comprising using an intramolecular Wittig reaction:

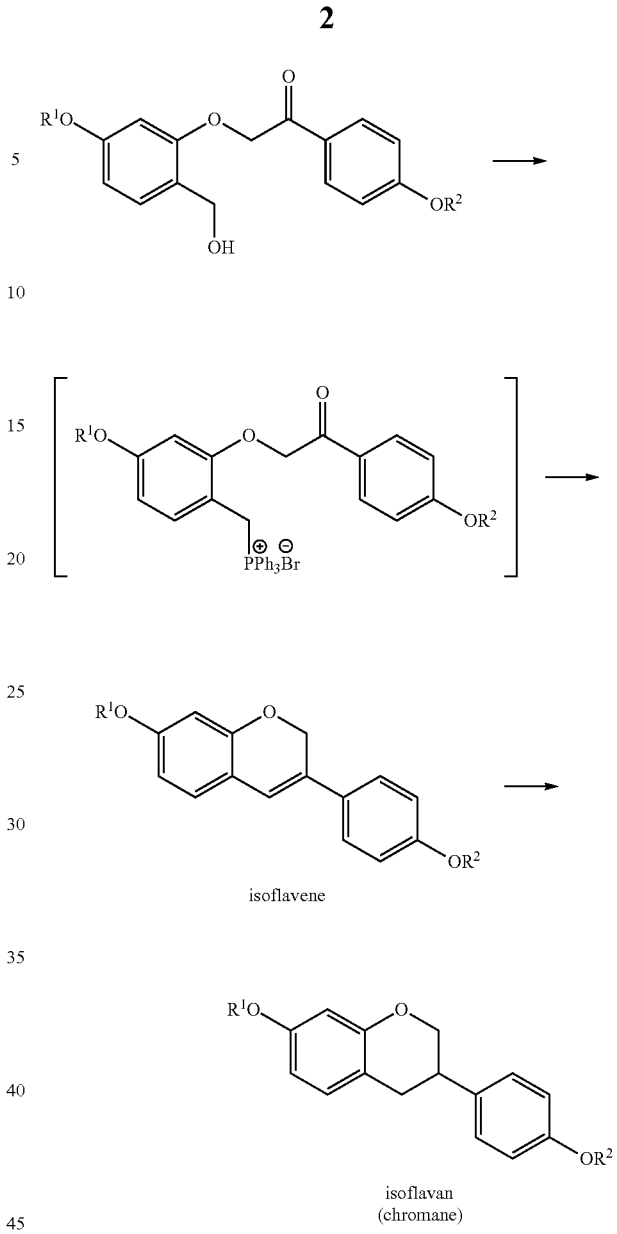

wherein $R^1$ and $R^2$ are either the same or independently H, alkyl, a phenolic protecting group, or a silyl derivative; and alkyl comprises a straight or branched alkane group having from 1 to 6 carbons.

In certain embodiments, the phenolic protecting group comprises one or more of: benzyl and methoxymethyl (MOM), and/or wherein the silyl derivative comprises a tertiary-butyl-dimethylsilyl (TBDMS) group.

In certain embodiments, the intramolecular Wittig reaction is done by first forming a phosphonium salt by treatment with triphenylphosphine hydrobromide in freshly distilled acetonitrile at ambient temperature, and then accomplishing the ring closure to the isoflav-3-ene product by placing the salt in t-BuOK/methanol.

In another aspect, there is provided herein a compound produced according to the above-described process.

In another aspect, there is provided herein a composition comprising a compound, pharmaceutically acceptable salt thereof made from an acid or a base, or a stereoisomer thereof, or combination thereof, made according to the above-described process, and a pharmaceutically acceptable carrier or diluent.

In certain embodiments, the compound is:

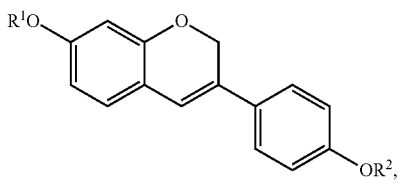

wherein $R^1$ and $R^2$ are either the same or independently H, alkyl, a phenolic protecting group, or a silyl derivative; and alkyl comprises a straight or branched alkane group having from 1 to 6 carbons; a pharmaceutically acceptable salt thereof made from an acid or a base, or a stereoisomer thereof. In certain embodiments, $R^1=R^2=$Bn or H.

In another aspect, there is provided herein a medical food product, a dietary supplement product, or ethical pharmaceutical product comprising a compound, pharmaceutically acceptable salt thereof made from an acid or a base, stereoisomer thereof, or combination thereof, made according to the above-described process. In certain embodiments, the medical food product, dietary supplement product, or ethical pharmaceutical comprises the compound:

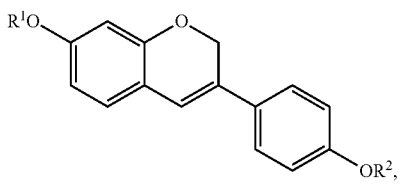

wherein $R^1$ and $R^2$ are either the same or independently H, alkyl, a phenolic protecting group, or a silyl derivative; and alkyl comprises a straight or branched alkane group having from 1 to 6 carbons; a pharmaceutically acceptable salt thereof made from an acid or a base, or a stereoisomer thereof.

In another aspect, there is provided herein a process for forming isoflavene and chromane analogs (P6, P7 and P8) comprising the process as shown in Scheme 1.

In another aspect, there is provided herein a process for preparing 2',4',7-trioxygenated-isoflavene and chromane compounds, comprising using an intramolecular Wittig reaction:

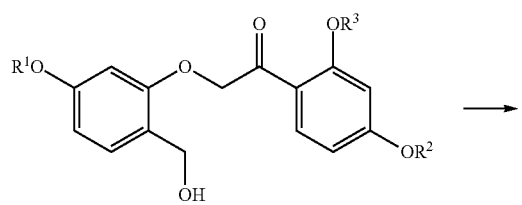

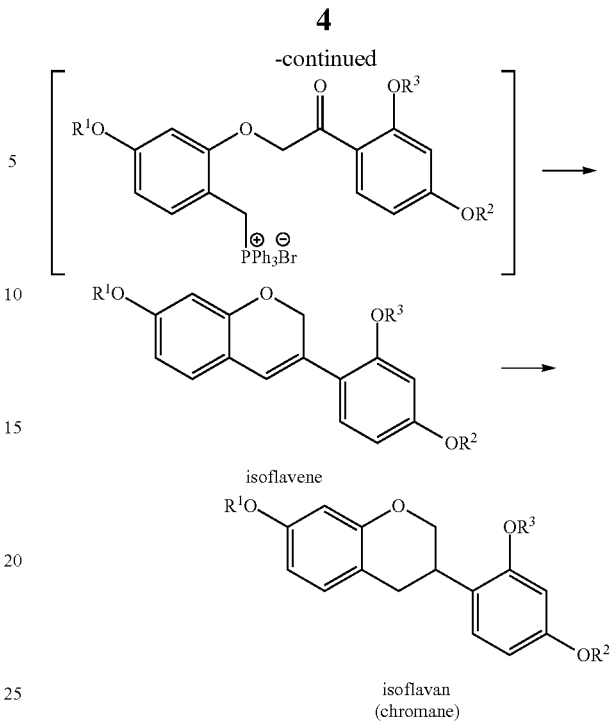

wherein $R^1$, $R^2$ and $R^3$ are either the same or independently H, alkyl, a phenolic protecting group, or a silyl derivative; and alkyl comprises a straight or branched alkane group having from 1 to 6 carbons.

In certain embodiments, the phenolic protecting group comprises one or more of: benzyl and methoxymethyl (MOM), and/wherein the silyl derivative comprises a tertiary-butyl-dimethylsilyl (TBDMS) group.

In certain embodiments, the intramolecular Wittig reaction is done by first forming a phosphonium salt by treatment with triphenylphosphine hydrobromide in freshly distilled acetonitrile at ambient temperature, and then accomplishing the ring closure to the isoflav-3-ene product by placing the salt in t-BuOK/methanol.

In another aspect, there is provided herein a compound produced according to the above-described process.

In another aspect, there is provided herein a composition comprising a compound, pharmaceutically acceptable salt thereof made from an acid or a base, or a stereoisomer thereof, or combination thereof, made according to the above-described process, and a pharmaceutically acceptable carrier or diluent.

In certain embodiments, the compound is:

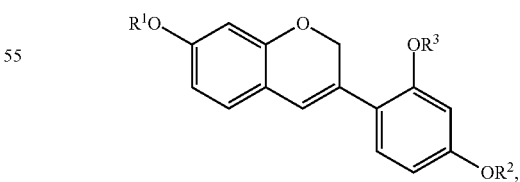

wherein $R^1$, $R^2$ and $R^3$ are either the same or independently H, alkyl, a phenolic protecting group, or a silyl derivative; and alkyl comprises a straight or branched alkane group having from 1 to 6 carbons; a pharmaceutically acceptable salt thereof made from an acid or a base, or a stereoisomer thereof. In certain embodiments, $R^1=R^2=R^3=$Bn or H.

In another aspect, there is provided herein a medical food product, a dietary supplement product, or ethical pharmaceutical product comprising a compound, pharmaceutically acceptable salt thereof made from an acid or a base, stereoisomer thereof, or combination thereof, made according to the above-described process.

In certain embodiments, the medical food product, dietary supplement product, or ethical pharmaceutical product is:

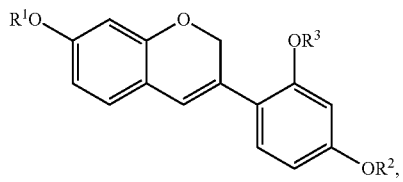

wherein $R^1$, $R^2$ and $R^3$ are either the same or independently H, alkyl, a phenolic protecting group, or a silyl derivative; and alkyl comprises a straight or branched alkane group having from 1 to 6 carbons; a pharmaceutically acceptable salt thereof made from an acid or a base, or a stereoisomer thereof.

In another aspect, there is provided herein a process for the syntheses of racemic vestitol (B5) and bolusanthin III (B6), as shown in Scheme 2.

In another aspect, there is provided herein a process for the synthesis of glycinol (GLO) comprising the process as shown in Scheme 3.

In another aspect, there is provided herein a process for the synthesis of glyceollins I and II (G1 and G2), as shown in Scheme 4.

In another aspect, there is provided herein a process for preparing 4',4'',7-trioxygenated-isoflavene and chromane compounds, comprising using an intramolecular Wittig reaction:

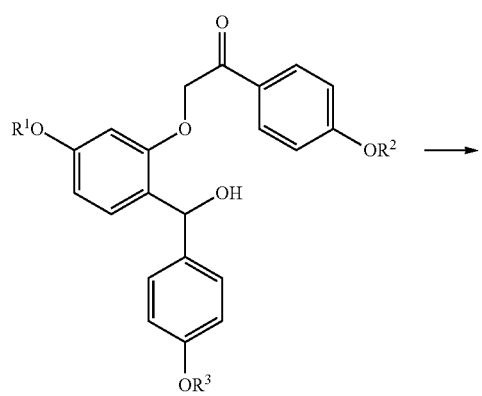

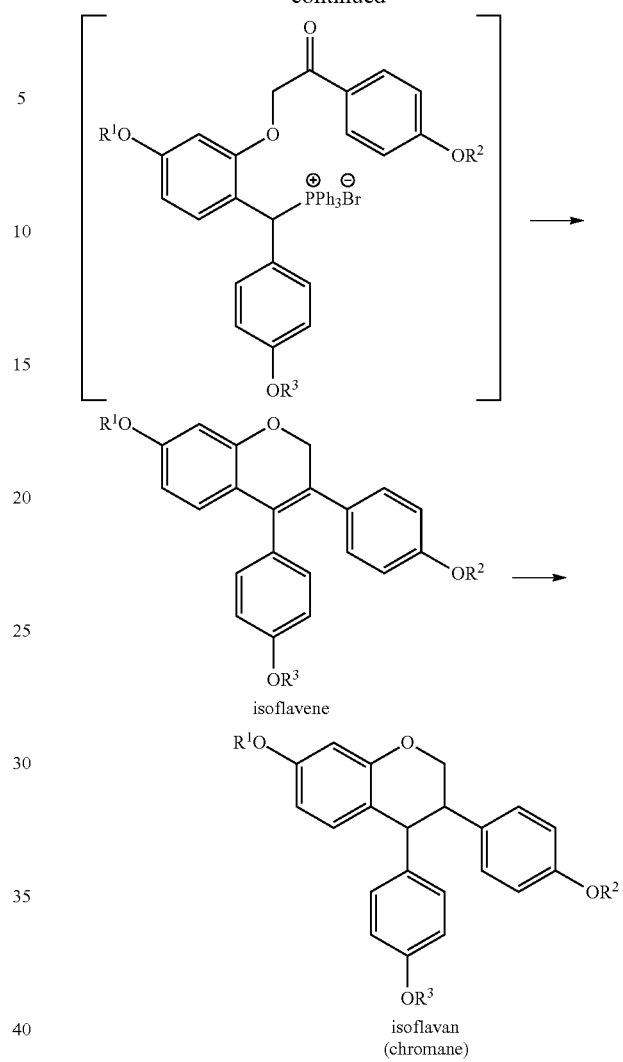

wherein $R^1$, $R^2$ and $R^3$ are either the same or independently H, alkyl, a phenolic protecting group or a silyl derivative; and alkyl comprises a straight or branched alkane group having from 1 to 6 carbons.

In certain embodiments, the phenolic protecting group comprises one or more of: benzyl and methoxymethyl (MOM), and/or wherein the silyl derivative comprises a tertiary-butyl-dimethylsilyl (TBDMS) group.

In certain embodiments, the intramolecular Wittig reaction is done by first forming a phosphonium salt by treatment with triphenylphosphine hydrobromide in freshly distilled acetonitrile at ambient temperature, and then accomplishing the ring closure to the isoflav-3-ene product by placing the salt in t-BuOK/methanol.

In another aspect, there is provided herein a compound produced according to the above-described process.

In another aspect, there is provided herein a composition comprising a compound, pharmaceutically acceptable salt thereof made from an acid or a base, or a stereoisomer thereof, or combination thereof, made according to the above-described process, and a pharmaceutically acceptable carrier or diluent.

In certain embodiments, the compound is:

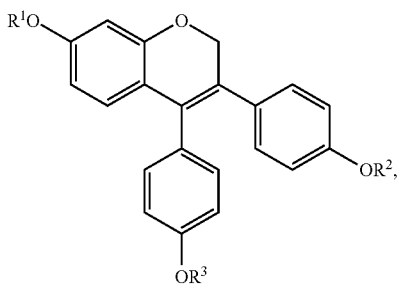

wherein $R^1$, $R^2$ and $R^3$ are either the same or independently H, alkyl, a phenolic protecting group, or a silyl derivative; and alkyl comprises a straight or branched alkane group having from 1 to 6 carbons; a pharmaceutically acceptable salt thereof made from an acid or a base, or a stereoisomer thereof. In certain embodiments, $R^1=R^2=R^3=$Bn or H.

In another aspect, there is provided herein a medical food product, a dietary supplement product, or ethical pharmaceutical product comprising a compound, pharmaceutically acceptable salt thereof made from an acid or a base, stereoisomer thereof, or combination thereof, made according to the above-described process.

In certain embodiments, the medical food product, dietary supplement product, or ethical pharmaceutical product is:

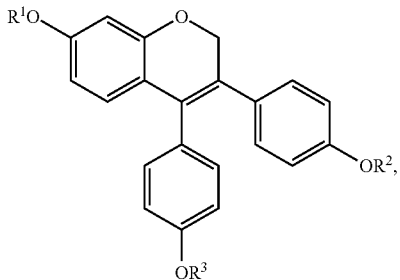

wherein $R^1$, $R^2$ and $R^3$ are either the same or independently H, alkyl, a phenolic protecting group, or a silyl derivative; and alkyl comprises a straight or branched alkane group having from 1 to 6 carbons; a pharmaceutically acceptable salt thereof made from an acid or a base, or a stereoisomer thereof.

In another aspect, there is provided herein a process for forming the isoflavene and chromane analogs (T4 and T5) comprising the process as shown in Scheme 5.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

FIG. 1—Scheme 1. Syntheses of Phenoxodiol (P7) and its Chromane Analog (P8).

FIG. 2—Scheme 2. Syntheses of Racemic Vestitol (B5) and Bolusanthin III (B6).

FIG. 3—Scheme 3. Synthesis of Glycinol (GLO).

FIG. 4—Scheme 4. Syntheses of Glyceollin I (G1) and Glyceollin II (G2).

FIG. 5—Scheme 5. Synthesis of Triphentriol (T5).

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The present invention provides individually pure GLY compounds, synthetic intermediates or selected analogs, to be used in various single-component product formulations. In certain embodiments, such single-components are useful as ingredients that can be added to enhance or fortify regular foods, medical foods or dietary supplement-related products.

In addition, the present invention provides for the production of a predetermined range of combined GLY-related compounds, wherein for the case of GLY I plus GLY II a ratio of about 5 to 1 can be achieved directly by synthesis, and wherein for all other cases, various ratios of various components can be achieved by selectively mixing the pure materials. These mixtures can be used in specific combination-component product formulations, or as specific combination-component ingredients that can be added to regular foods, medical foods or dietary supplement-related products.

It is to be understood that the accompanying figures that convey specific chemical synthesis schemes and analytical data descriptions are intended to generally encompass the cited references and their applicable organic synthesis or biological testing methodologies within the distinct context of the GLYs and the GLYs' immediately accessible synthetic intermediates.

In a particular embodiment, there is provided a method using an intramolecular Wittig process for the production of variously substituted isoflavene natural product analogs. In particular, described herein are a specific methods for preparing these analogs, as well as for preparing glyceollins I, II (GLYs I, II) and glycinol (GLO).

Distinct from the prior methods of synthesizing isoflavenes, the inventors herein have now developed a process that does not require thallium. The latter is highly toxic to humans and then becomes an environmental burden after its use in such reactions. In addition, the yields for the process described herein are much more consistent and tend to be somewhat higher than for the thallium-mediated step, and thus it is more conducive to devising manufacturing scale processes that can have reduced costs.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

Example 1

Preparation of Phenoxodiol (P7) and its Chromane Analog (P8) (Scheme 1)

4-Benzyloxy-2-hydroxy-benzaldehyde (P1)

Anhydrous sodium bicarbonate (1 g, 12 mmol) was added to a solution of 2,4-dihydroxybenzaldehyde (1.38 g, 10 mmol) in 50 mL of acetonitrile and the mixture was stirred for 1 hour at RT. Benzylbromide (1.2 mL, 10 mmol) was added and the mixture was refluxed for 6 hours. After disappearance of the reactant (TLC), the reaction was poured into ice water with vigorous stirring. A white solid precipitated and it was recrystallized from methanol (ca. 40 mL) to obtain (1.82 g, 80 of P1 as a white powder: mp 78-80° C.; TLC $R_f$ 0.88 in toluene:methanol (10:1); $^1$H NMR (600 MHz, acetone-$d_6$) δ 11.41 (s, 1H, OH), 9.81 (s, 1H, CHO), 7.67 (d, 1H, J=8.4 Hz, Ar—H6), 7.45-7.35 (m, 5H, $C_6H_5$), 6.70 (dd, 1H, $^2$J=8.4 Hz, $^3$J=2.4 Hz, Ar—H5), 6.56 (d, 1H, J=1.8 Hz, Ar—H3), 5.24 (s, 2H, $PhCH_2$).

4-Benzyloxy-salicylalcohol (P2). To an ice cooled suspension of 4-benzyloxy-2-hydroxybenzaldehyde (P1) (2.28 g, 10 mmol) in 10 mL of methanol was slowly added sodium borohydride (0.38 g, 10 mmol). After addition of sodium borohydride, a clear solution was obtained. The reaction was stirred at 0° C. for 20 minutes followed by stirring at RT for 10 minutes. The solvent was evaporated under vacuum. To this solid residue was carefully added 0.1 N $H_2SO_4$ until the pH dropped to 6.5 with vigorous stirring. Additional water (ca. 100 mL) was added with continuous stirring which then caused the product to precipitate. The solid was filtered and copiously washed with water to remove all traces of acid (last wash pH≧7). The solid was immediately vacuum dried to obtain (1.75 g, 76%) of P2 as a white solid: mp 88-90° C.; TLC, $R_f$ 0.29, in hexanes:EtOAc (2:1); $^1$H NMR (600 MHz, DMSO-$d_6$) δ, 9.36 (s, 1H, Ph-OH), 7.43-7.32 (m, 5H, $C_6H_5$), 7.13 (d, 1H, J=8.4 Hz, Ar—H6), 6.44-6.41 (m, 2H, Ar—H5/Ar—H3), 5.01 (s, 2H, $PhCH_2$), 4.8 (t, 1H, $CH_2OH$), 4.39 (s, 2H, $OHCH_2$).

4-Benzyloxy-acetophenone (P3). Anhydrous potassium carbonate (2.76 g, 20 mmol) was added to a solution of 4-hydroxy-acetophenone (1.36 g, 10 mmol) in 60 mL of acetone and the mixture was stirred for 1 hour at RT. Benzylbromide (1.2 mL, 10 mmol) was added and the mixture was refluxed for 12 hours. After disappearance of the reactant (TLC), the white solid was filtered and filtrate was evaporated to give (2.03 g, 90%) product P3 as crystalline white solid. $^1$H NMR (400 MHz, $CDCl_3$) δ, 7.94 (d, 2H, J=8.8 Hz, Ar-2,6), 7.43-7.40 (m, 5H, $C_6H_5$), 7.01 (d, 2H, J=8.8 Hz, Ar-3,5), 5.14 (s, 2H, $PhCH_2$), 2.6 (s, 3H, $COCH_3$).

1-(4-Benzyloxy-phenyl)-2-iodo-ethanone (P4). 4-Benzyloxy-acetophenone (P3) (0.226 g, 1 mmol) was dissolved in 1 mL $CH_2Cl_2$ and 5 mL of anhydrous methanol. Selectfluor™ (0.230 g, 0.6 mmol) and elemental iodine (0.126 g, 0.5 mmol) were added and the mixture stirred at room temperature for 12 hours. Then 15 mL of chloroform was added and an ash colored solid precipitated. The precipitate was filtered and the filtrate was extracted with 10% aqueous sodium thiosulfate solution (5×20 mL) until the organic layer became lemon yellow. The organic layer was evaporated under vacuum to obtain a yellowish oily residue which was redissolved in methanol:acetone (ca. 20 mL:2 mL) and refrigerated overnight. The desired product precipitated while the filtrate retained side products having iodination on the aromatic ring and di-iodination at the alpha-carbon. The product was filtered and dried to obtain (0.253 g, 72%) of P4 as a yellow powder. $^1$H NMR (400 MHz, $CDCl_3$) δ, 7.97 (dd, 2H, $^2$J=6.8 Hz, $^3$J=2 Hz), 7.42-7.26 (m, 5H, $C_6H_5$), 7.02 (dd, 2H, $^2$J=7.2 Hz, $^3$J=2 Hz), 5.14 (s, 2H, $PhCH_2$), 4.13(s, 2H, $CH_2I$).

2-(5-Benzyloxy-2-hydroxymethyl-phenoxy)-1-(4-benzyloxy-phenyl)-ethanone (P5). Potassium carbonate (1.65 g, 12 mmol) was added to a solution of 1-(4-benzyloxy-phenyl)-2-iodo-ethanone (P4) (3.52 g, 10 mmol) and 4-benzyloxy-salicylalcohol (P2) (2.53 g, 11 mmol) were in 100 mL of dry acetone and the mixture was refluxed for 4 hr. After completion of reaction (TLC), the solvent was evaporated and the residue extracted with EtOAc:water (3×200 mL). The organic layers were combined, dried over sodium sulfate and evaporated. The residue was dissolved and recrystallized from dichloromethane: methanol ca. (10:50 mL) to give (3.13 g, 69%) yellowish white solid product P5. $^1$H NMR (400 MHz, $CDCl_3$) δ, 7.91(d, 2H, J=8.8 Hz, Ar—H2/H6), 7.44-7.29(m, 10H, 2×$C_6H_5$), 7.19 (d, 1H, J=8 Hz, Ar—H3'), 7.03 (d, 2H, J=8.8 Hz, Ar—H3/H5), 6.55(dd, 1H, $^2$=8.4 Hz, $^3$=2.4 Hz, Ar—H4'), 6.49(d, 1H, J=2.4 Hz, Ar—H6'), 5.29 (s, 2H, $PhCH_2$), 5.13(s, 2H, $PhCH_2$), 5.01 (s, 2H, H-2), 4.74(s, 1H, $OHCH_2$), 4.68 (s, 2H, $CH_2OH$).

7-Benzyloxy-3-(4-benzyloxy-phenyl-2-H-chromene (P6). To a solution of 2-(5-benzyloxy-2-hydroxymethyl-phenoxy)-1-(4-benzyloxy-phenyl)-ethanone (P5) (4.54 g, 10 mmol) in 100 mL of $CH_3CN$ was added triphenyl phosphine hydrobromide (3.77 g, 11 mmol) and the suspension was heated at 60° C. for about 2 hours. After disappearance of starting material (TLC), solvent was evaporated to give yellowish phosphonium salt. The solid was dissolved in 100 mL of anhydrous methanol followed by addition of potassium tert-butoxide (2.46 g, 22 mmol). The suspension was refluxed for 6 hours till completion of reaction (TLC). The solvent was evaporated and the residue extracted with EtOAc:water (3×200 mL). The organic layers were combined, dried over sodium sulfate and evaporated. The residue was chromatographed over silica using hexanes:DCM (4:1) to give (3.08 g, 68%) of yellowish white solid product P6. $^1$H NMR (600 MHz, Acetone-d6) δ, 7.48-7.4 (m, 12H, Ar—H2'/H6', 2×$C_6H_5$), 7.06 (m, 3H, Ar—H3'/H5', Ar—H5), 6.85(s, 1H, H-4), 6.59(dd, 1H, Ar—H5), 6.51(d, 1H, Ar—H8), 5.16(s, 2H, $PhCH_2$), 5.13 (s, 2H, $PhCH_2$), 5.12(s, 2H, O—$CH_2$).

3-(4-Hydroxy-phenyl)-2H-chromen-7-ol (P7). To a solution of 7-benzyloxy-3-(4-benzyloxy-phenyl)-2-H-chromene (P6) (0.840 g, 2 mmol) in 20 mL of anhyd $CH_2Cl_2$ (DCM) at −78° C., 4.2 mL (4.2 mmol) of 1M solution of $BBr_3$ in $CH_2Cl_2$ was added dropwise. After stirring for 10 min, TLC indicated disappearance of starting material. The reaction was quenched with 2 mL of MeOH. The solvents were evaporated and residue extracted with EtOAC:water (1×100 mL). The organic layers were combined, dried over sodium sulfate and evaporated to give beige solid, which was recrystallized from hexane: EtOAc (1:1) to give (0.30 g, 63%) reddish white solid P7. $^1$H NMR (600 MHz, Acetone-d6) δ,7.35 (d, 2H, J=8.4 Hz, Ar—H2'/H6'), 6.95 (d, 1H, J=7.8 Hz, Ar—H5), 6.85 (d, 2H, J=8.4 Hz, Ar—H3'H5'), 6.39, (dd, 1H, $^2$J=7.8 Hz, $^3$J=2.4 Hz), 6.31 (d, 1H, $^3$J=2.4 Hz), 5.06 (s, 2H, O—$CH_2$).

3-(4-Hydroxy-phenyl)-chroman-7-ol (P8). To a solution of 3-(4-hydroxy-phenyl)-2H-chromen-7-ol (P7) (0.241 g, 1 mmol) in MeOH was added 10% Pd—C (0.050 g). This reaction mixture was hydrogenated at room temperature under 2 atm (30 psi) of $H_2$ pressure for ca. 6 hours. After the disappearance of starting material (TLC), the catalyst was filtered through a pad of celite. The celite-pad was washed with 10 mL of THF then 2×10 mL of MeOH. The solution was filtered once more through filter paper and evaporated to obtain the brownish solid residue which was chromatographed over silica gel using $CH_2Cl_2$:MeOH (6:1) to get (0.169 g, 70%) reddish white solid P8. $^1H$ NMR (600 MHz, Acetone-d6) δ, 7.08 (d, 2H, J=8.4 Hz, Ar—H2'/H6'), 6.82 (d, 1H, J=7.8 Hz, Ar—H5), 6.80 (d, 2H, J=8.4 Hz, Ar—H3'/H5'), 6.35, (dd, 1H, $^2J$=7.8 Hz, $^3J$=2.4 Hz), 6.27 (d, 1H, $^3J$=2.4 Hz), 4.15 (m, 1H, O—CH), 3.88 (t, 1H, J=10.8 Hz, O—CH), 3.0 (m, 1H, 3-CH), 2.9 (m, 2 H, 4-$CH_2$).

Example 2

Preparation of Racemic Vestitol (B5) and Bolusanthin III (B6) (Scheme 2)

1-(2'-Benzyloxy-4'-methoxy)phenyl-2-iodoethanone (B1). To a solution of 4-methoxy-2-hydroxyacetophenone (5.0 g, 30 mmol) in $CH_3CN$ (80 mL), $K_2CO_3$ (5.0 g, 36 mmol) benzyl bromide (5.0 g, 29 mmol) were added. The reaction mixture was allowed to stir under refluxing conditions. The reaction progress was followed by TLC and $^1H$ NMR. After 24 h the solvents were evaporated under vacuum and the off white residue was dissolved in EtOAc and washed with 2 M sodium hydroxide, 0.1 M HCl, $H_2O$, and brine. After drying over anhyd $Na_2SO_4$ and then filtration, the volatiles were evaporated under vacuum to obtain 2-benzyloxy-4-methoxy-acetophenone B1a (7.4 g, 28.8 mmol, 96%) as white solid: mp 84-88° C.; TLC $R_f$=0.40 [EtOAc/hexanes (1:3)]; $^1H$ NMR ($CDCl_3$, 600 MHz) δ 7.85 (1H, d, J=8.4 Hz), 7.40 (5H, m), 6.53 (2H, m), 5.13 (2H, s), 3.83 (3H, s), 2.56 (3H, s); $^{13}C$ NMR ($CDCl_3$, 150 MHz) δ 197.8, 164.3, 160.1, 135.9, 132.7, 128.7, 128.2, 127.6, 121.4, 105.3, 99.4, 70.6, 55.5, 32.2.

To a solution of B1a (22.7 g, 88.6 mmol) in anhyd $CH_2Cl_2$ (100 mL) and anhyd MeOH (500 mL), Selectfluor™ (18.9 g, 53.3 mmol) was added followed by addition of elemental iodine (11.25 g, 44.3 mmol). The reaction mixture was stirred for 20 h. The progress of reaction was monitored by TLC and $^1H$ NMR. After completion, reaction mixture was filtered and the ppt was washed with $CH_2Cl_2$. The combined filtrate was evaporated under vacuum and the solid residue was dissolved in $CH_2Cl_2$ (200 mL) and washed with freshly prepared 10% sodium thiosulfate solution (3×125 mL). The organic layer was dried over anhyd $Na_2SO_4$, filtered and evaporated to dryness. The solid residues were purified by recrystallization from $Me_2CO$/MeOH (1:10, 100 mL) to obtain B1. (28.4 g, 74.3 mmol, 84%) as yellowish crystals: mp 96-100° C.; TLC $R_f$=0.54 [EtOAc/hexanes (1:3)]; $^1H$ NMR ($CDCl_3$, 600 MHz) δ 7.91 (1H, d, J=9.0 Hz), 7.44 (5H, m), 6.57 (1H, dd, J=9.0 Hz), 6.53 (1H, d, J=2.4 Hz), 5.17 (2H, s), 4.40 (2H, s), 3.84 (3H, s); $^{13}C$ NMR ($CDCl_3$, 150 MHz) 165.1, 159.7, 135.5, 134.1, 128.84, 128.83, 128.5, 127.9, 117.4, 106.0, 99.3, 71.0, 55.6, 9.9; Anal. (%) calcd for $C_{16}H_{15}IO_3 \cdot 0.5 H_2O$, C 49.13, H 4.12, found C 48.82, H 3.78.

4-Benzyloxysalicyl alcohol (B2). To a solution of 2,4-dihydroxybenzaldehyde (100 g, 0.72 mol) in $CH_3CN$ (1.5 L), $NaHCO_3$ (72.0 g, 0.86 mol) and benzyl bromide (145.4 g, 0.85 mol) were added and the reaction mixture was stirred under reflux. The reaction progression was followed by TLC and on completion the reaction mixture was cooled to room temperature and filtered. The organic solvents were evaporated under vacuum. The off white residue was recrystallized from MeOH to obtain 4-benzyloxy-2-hydroxybenzaldehyde (B2a) (140 g, 0.61 mol) in 85% yield: mp 77-79° C. [lit.$^{42}$ mp 78-80° C.); TLC $R_f$ 0.73 [EtOAc/hexanes (1:2)]; $((CD_3)_2CO$, 600 MHz) δ 11.50 (1H, s), 9.88 (1H, br), 7.67 (1H, d, J=5.4 Hz), 7.50 (2H, d, J=7.2), 7.41 (2H, m), 7.36 (1H, m), 6.71 (1H, m), 6.57 (1H, s), 5.24 (2H, s).

To a mixture of B2a (6 g, 28.2 mmol) in anhyd EtOH (120 mL), sodium borohydride (850 mg) was added portion-wise at 0° C. On addition of sodium borohydride the reaction mixture turned clear with evolution of gases. The reaction mixture was allowed to stir at 0° C. for 1 h and then for 8-10 h at rt. The reaction progression was followed by TLC. After completion, the reaction mixture was reduced to one-fourth of its original volume and then was neutralized with 0.1 M sulfuric acid. The precipitates were formed on addition of $H_2O$ (ca. 500 mL). The ppt was filtered and recrystallized from toluene to obtain B2 (3.8 g, 16.5 mmol, 58%) as off white crystals: nip 89.0-92.0 [lit.$^{42}$ mp 88.0-90.0° C.]; TLC $R_f$=0.33 [EtOAc/hexanes (1:2)]; $^1H$ NMR (DMSO-$d_4$, 400 MHz) δ 9.36 (1H, br), 7.36 (5H, m), 7.12 (1H, d, J=8.0 Hz), 6.42 (2H, m), 5.01 (2H, s), 4.80 (1H, br), 4.38 (2H, s).

1-(2'-Benzyloxy-4'-methoxy)phenyl-2-(6'-benzyloxy-2'-hydroxymethyl)phenyl-ethanone (B3). To a solution of α-iodo ketone B1 (0.28 g, 0.74 mmol) and salicyl alcohol B2 (0.19 g, 0.82 mmol) in $Me_2CO$ (15 mL), $K_2CO_3$ (0.14 g, 0.98 mmol) was added under a flow of $N_2$. The reaction mixture was refluxed for 16-18 h. Reaction progress was monitored by TLC. After completion, the solvents were evaporated and the solid residue was dissolved in EtOAc (120 mL) and was washed with 1 M NaOH, $H_2O$, brine, dried over anhyd $Na_2SO_4$ and evaporated to dryness under vacuum to obtain. The solid residue was purified using flash column chromatography to obtain B3 (0.28 g, 0.57 mmol, 78%) as off-white solid: mp 150-153° C.; TLC $R_f$=0.17 [EtOAc/hexanes (1:2)]; $^1H$ NMR $((CD_3)_2CO$, 600 MHz) δ 7.89 (1H, d, J=8.4 Hz), 7.45 (10H, m), 7.22 (1H, d, J=9.0 Hz), 6.83 (1H, d, J=2.4 Hz), 6.68 (1H, dd, J=2.4, 9.0 Hz), 6.56 (1H, dd, J=2.4, 8.4 Hz), 6.26 (1H, d, J=2.4 Hz), 5.33 (2H, s), 5.21 (2H, s), 4.99 (2H, s), 4.98 (2H, d, J=6.6 Hz), 4.15 (1H, t, J=6.6 Hz), 3.90 (3H, s); $^{13}C$ NMR $((CD_3)_2CO$, 100 MHz) δ 193.7, 166.3, 161.7, 160.1, 158.0, 138.2, 137.0, 133.2, 129.6, 129.5, 129.3; 129.2, 129.1, 128.6, 124.4, 118.9, 107.5, 106.0, 101.0, 99.8, 74.6, 71.7, 70.5, 60.9, 56.1; Anal. (%) calcd for $C_{30}H_{28}O_6 \cdot 0.25H_2O$, C 73.68, H 5.87, found C 73.33, H 5.71.

2',7-Dibenzyloxy-4'-methoxyisoflav-3-ene (B4). To a suspension of B3 (97 mg, 0.2 mmol) in anhyd $CH_3CN$ (4 mL), $PPh_3 \cdot HBr$ (70 mg, 0.2 mmol) was added under a flow of $N_2$. The reaction mixture was stirred at rt and was followed The reaction progress was monitored by TLC. After completion, solvents were evaporated under vacuum to obtain an off-white residue which was directly used in the next step without further purification.

To a solution the above phosphonium salt in anhyd MeOH (15 mL), t-BuOK (45 mg, 0.4 mmol) was added under a flow of $N_2$. The reaction mixture was refluxed for 16-20 h. The reaction progress was monitored by TLC. After completion, the mixture was reduced to one-third of original volume under vacuum and was filtered. The precipitates were dissolved in $CH_2Cl_2$ (30 mL). The organic phase was washed with $H_2O$, brine, dried over anhyd $Na_2SO_4$ and evaporated to dryness under vacuum to obtain B4 (50 mg, 0.11 mmol, 70% over 2 steps) as off-white solid: mp 119-122° C.; TLC $R_f$=0.65 [EtOAc/hexanes (1:2)]; $^1H$ NMR $((CD_3)_2CO$, 600 MHz) δ 7.41 (10H, m), 7.28 (1H, d, J=8.4 Hz), 7.01 (1H, d, J=7.8 Hz), 6.70 (1H, d, J=2.4 Hz), 6.60 (1H, s), 6.57 (2H, m, H6), 6.46 (1H, d, J=1.8 Hz), 5.16 (2H, s), 5.10 (2H, s), 4.93 (2H, s), 3.8 (3H, s); $^{13}C$ NMR $((CD_3)_2CO$, 150 MHz) δ 161.7, 160.3, 158.2, 155.5, 138.2, 137.8, 130.0, 129.9, 129.4, 129.3, 129.2, 128.7, 128.6, 128.5, 128.3, 128.2, 121.5, 121.4, 118.1, 108.9, 106.3, 102.8, 100.5, 71.0, 70.4, 68.9, 55.6, 3.4; Anal. (%) calcd for $C_{30}H_{26}O_4 \cdot 0.5H_2O$, C 78.41, H 5.92, found C 78.30, H 5.69.

Racemic Vestitol (B5). To a solution of B4 (50 mg, 0.11 mmol) in EtOAc (15 ml) at 0° C., 10% w/w Pd/C (15-20 mg) was added. The mixture was stirred at rt under hydrogen atmosphere (35 psi) and was followed by TLC. After completion, the reaction mixture was passed through a pad of Celite and was washed with EtOAc (3×10 mL). The solvents were dried over anhyd $Na_2SO_4$ and evaporated under vacuum and the residue was further purified using flash column chromatography [EtOAc/hexanes (1:1)] to obtain B5 (25 mg, 90 μmol, 84%) as off-white powder: mp 172-179 °C.; TLC $R_f$=0.44 [EtOAc/hexanes (1:1)]; $^1$H NMR (($CD_3)_2CO$, 600 MHz) δ 8.6 (2H, br), 7.05 (1H, d, J=8.4 Hz), 6.88 (1H, d, J=8.4 Hz), 6.50 (1H, d, J=2.4 Hz), 6.42 (1H, dd, J=2.4, 8.4 Hz), 6.35 (1H, dd, J=2.4,8.4 Hz), 6.27 (1H, d, J=2.4 Hz), 4.23 (1H, m), 3.97 (1H, t, 10.2 Hz), 3.71 (3H, s), 3.47 (1H, m), 2.96 (1H, m), 2.79 (1H, m); $^{13}$C NMR (($CD_3)_2CO$, 100 MHz) δ 160.3, 157.4, 156.6, 156.0, 130.9, 128.6, 120.8, 114.2, 108.6, 105.5, 103.5, 102.4, 70.4, 55.2, 32.5, 30.9; Anal. (%) calcd for $C_6H_{16}O_4$, C 70.57, H 5.92, found C 70.22, H 5.98.

Bolusanthin III (B6). To a solution of B4 (0.45 g, 0.1 mmol) and pentamethylbenzene (0.158 g, 1 mmol) in anhyd $CH_2Cl_2$ (30 mL) at −78° C., $BCl_3$ (0.2 mmol) was dropwise added under $N_2$. The reaction mixture was stirred at −78° C. and after 15-20 min the reaction was quenched with 20 mL of $CHCl_3$/MeOH (10:1) mixture. The resulting mixture was warmed to rt. The organic solvents were evaporated under vacuum. The residues were purified by column chromatography [Silica gel 35 mm dia, 8 inch thick, EtOAc/hexanes (1:2)] to obtain B6 (0.17 g, 0.61 mmol, 61%) as brownish solid: mp 150-154° C.; TLC $R_f$=0.48 [EtOAc/hexanes (1:2)]; $^1$H NMR ($CD_3OD$, 600 MHz) δ 7.14 (1H, d, J=8.4 Hz), 6.88 (1H, d, J=8.4 Hz), 6.53 (1H, s), 6.42 (1H, dd, J=2.4, 8.4 Hz), 6.37 (1H, d, J=2.4 Hz), 6.33 (1H, dd, J=2.4, 8.4 Hz), 6.24 (1H, d, J=1.8 Hz), 4.95 (2H, s), 3.75 (3H, s); $^{13}$C NMR ($CD_3OD$, 150 MHz) δ 161.8, 159.1, 157.3, 155.9, 130.1, 130.0, 128.4, 121.4, 119.9, 117.6, 109.4, 106.1, 103.4, 102.4, 69.2, 55.6; Anal. (%) calcd for $C_{16}H_{14}O_4 \cdot 0.1 H_2O$, C 70.63, H 5.26, found C 70.42, H 5.20.

Example 3

Preparation of Glycinol (GLO) (Scheme 3)

4-Benzyloxysalicyl alcohol (G3). To a solution of the 2,4-dihydroxybenzaldehyde (100 g, 0.67 mol) in $CH_3CN$ (1 L), BnBr (112.4 g, 0.67 mol) and $NaHCO_3$ (90.8 g, 0.67 mol) were added. The reaction mixture was refluxed for 48 h and was monitored by TLC. Upon completion, the white precipitate was filtered and the filtrate was evaporated under vacuum. The residue was dissolved in MeOH (500 mL) and was precipitated at 0° C. The precipitates were further recrystallized from MeOH to obtain 4-Benzyloxy-2-hydroxybenzaldehyde (G3a) (127.5 g, 0.56 mol, 84%) as an off-white solid: mp 80-82C (Lit.[10] 78-80° C.); $^1$H NMR (DMSO, 400 MHz) δ 10.99 (1H, s), 9.99 (1H, s), 7.37 (5H, m), 6.61 (1H, m), 6.54 (1H, d), 5.15 (2H, s).

To a solution of the benzaldehyde G3a (127.5 g, 0.52 mol) in MeOH (1 L) at 0 ° C., $NaBH_4$ (16 g, 0.42 mol) was added. The reaction mixture was stirred for 18 h at rt. Reaction progress was monitored by TLC. Upon completion, the reaction mixture was reduced to one-fourth volume and was treated with 0.5 N aq $H_2SO_4$ to adjust pH to about 6-7 followed by addition of $H_2O$ (1 L). Upon vigorous stirring white precipitate formed. After filtration, the precipitate was lyophilized, washed using chilled toluene (ca. −50° C.) and dried under vacuum to obtain G3 (89 g, 0.38 mol, 73%) as an off-white solid: mp 86-88° C. (Lit.[8] 88-90° C.); $^1$H NMR (DMSO, 400 MHz) δ 9.33 (1H, s), 7.35 (5H, m,) 7.08 (1H, d, J=8.4 Hz), 6.42 (2H, m), 5.01 (2H, s), 4.80 (1H, m), 4.39 (2H, s).

2-Benzyloxy-4-methoxymethylenoxyacetophenone (G4a). Synthesis of 2-hydroxy-4-methoxymethylenoxyacetophenone (procedure A): To a solution of dimethoxymethanal (150.5 g; 1.97 mol, 175 mL) and $Zn(OAc)_2$ (43.88 mg, 0.24 mmol) in EtOAc (350 mL), $CH_3COCl$ (154.7 g, 1.97 mol) was added over 2-3 h. The reaction mixture was stirred for an additional 2-3 h and then cooled to 0° C. A solution of 2,4-dihydroxyacetophenone (200.0 g, 1.31 mol) in EtOAc (615 mL) was then added slowly, followed by dropwise addition of Hunig's base (211.6 g, 1.63 mol). The reaction mixture was stirred for 18 h while being monitored by TLC. After completion, $H_2O$ (300 mL) was added and the mixture further stirred for 1 h. The organic phase was washed with 1M NaOH, brine and dried over anhyd $Na_2SO_4$. Solvents were evaporated under vacuum to obtain 2-hydroxy-4-methoxymethylenoxyacetophenone as a yellowish oily residue which was utilized directly in the next step.

Synthesis of 2-hydroxy-4-methoxymethylenoxyacetophenone (procedure B): Oven-dried potassium carbonate (0.17 g, 1.2 mmol) was added to an ice cooled solution of 2,4-dihydroxyacetophenone (0.15 g, 1 mmol) in 5 mL of $Me_2CO$. MOMCl (0.15 mL, 2 mmol) was added dropwise and the mixture was stirred at 0° C. for an hour. The temperature of the reaction was gradually allowed to come to rt and was further stirred for 24 h, after which it was quenched with $H_2O$ (ca. 10 mL). The $Me_2CO$ was evaporated under vacuum. The remaining water layer was extracted with $CH_2Cl_2$ (2×10 mL). The organic layers were combined, dried over anhyd $Na_2SO_4$ and evaporated to obtain 0.156 g of 2-hydroxy-4-methoxymethylenoxyacetophenone as an oily residue which was used directly in the next step without further purification.

To a solution of 2-hydroxy-4-methoxymethylenoxyacetophenone (128.3 g) in $Me_2CO$ (1.3 L), BnBr (168.6 g, 0.98 mol) and $K_2CO_3$ (96.74 g) were added under a flow of $N_2$. The reaction mixture was stirred under reflux while progress was monitored by TLC. After completion, the mixture was filtered and solvents were evaporated under vacuum. The product was recrystallized from MeOH to obtain 2-benzyloxy-4-methoxymethylenoxy-acetophenone (G4a) (249.0 g, 0.97 mol, 74% in 2 steps) as off-white crystals: mp 71-73° C. (lit.[8] 70-71° C.); TLC $R_f$=0.63 [EtOAc/hexanes (1:2)]; $^1$H NMR ($CDCl_3$, 600 MHz) δ 7.82 (1H, d, J=8.4 Hz), 7.40 (5H, m), 6.68 (2H, m), 5.19 (2H, s), 5.14 (2H, s), 3.47 (3H, s), 2.55 (3H, s).

1-(2'Benzyloxy-4'-methoxymethylenoxy)phenyl-2-iodoethanone (G4). To a solution of acetophenone G4a (124.26 g, 0.43 mol) in anhyd $CH_2Cl_2$ (280 mL) and anhyd MeOH (1.7 L), Selectfluor™ (100 g, 0.26 mol) was added followed by elemental $I_2$ (49.88 g, 0.22 mol) under a flow of $N_2$. The reaction mixture was stirred for 24 h. Reaction progress was monitored by TLC and $^1$H NMR. After completion, the mixture was filtered and the precipitate was washed extensively with $CH_2Cl_2$. The combined organic phase was evaporated under vacuum at 25-30° C. The residue was again dissolved in $CH_2Cl_2$. The organic layer was washed with freshly prepared $Na_2S_2O_3$ solution (10% w/v), dried over anhyd $Na_2SO_4$ and evaporated under vacuum. The residue was recrystallized from MeOH to obtain G4 (140.1 g, 0.34 mol, 79%) as yellowish crystals: mp 76-78° C. (lit.[8] 66-68° C.); TLC $R_f$=0.65 [EtOAc/hexanes (1:2)]; $^1$H NMR ($CDCl_3$, 600 MHz) δ 7.88

(1H, d, J=9.6 Hz), 7.49 (2H, m), 7.41 (3H, m), 6.71 (2H, m), 5.20 (2H, s), 5.17 (2H, s), 4.40 (2H, s), 3.48 (3H, s).

2-(5'-Benzyloxy-2'-hydroxymethyl)phenoxy-1-(2'-benzyloxy-4'-methoxy-methylenoxy)phenylethanone (G5). To a solution of salicyl alcohol G3 (107.5 g, 0.46 mol) and α-iodo ketone G4 (115.7 g, 0.28 mol) in $Me_2CO$ (1.4 L), $K_2CO_3$ (46.32 gm, 0.34 mol) was added. The reaction mixture was stirred at reflux for 18-20 h. Reaction progress was followed by TLC and $^1H$ NMR. After completion, solvents were evaporated under vacuum and the residue dissolved in $EtOAc/H_2O$ (1:1) mixture. The organic layer was washed with 0.1 M HCl, saturated $NaHCO_3$, $H_2O$, brine, dried over anhyd $Na_2SO_4$ and evaporated to dryness under vacuum to obtain, dried over anhyd $Na_2SO_4$ and evaporated under vacuum. The solid residue was recrystallized from EtOAc/hexane (700 mL, 1:1) to obtain G5 (107.8 g, 0.21 mol, 72%) as a white solid: mp 122-124° C. [lit.[8] 115-118° C.]; TLC $R_f$=0.3 [EtOAc/Hexane (1:2)]; $^1H$ NMR (($CD_3)_2CO$ 400 MHz) δ 7.87 (1H, d, J=8.8 Hz), 7.64 (2H, d, J=7.6 Hz), 7.41 (6H, m), 7.33 (1H, m), 7.24 (2H, m), 6.93 (1H, d, J=2 Hz), 6.77 (1H, dd, J=2, 8.8 Hz), 6.56 (1H, dd, J=2.4, 8.4 Hz), 6.26 (1H, m), 5.32 (4H, s), 5.20 (2H, s), 4.98 (2H, s), 4.57 (2H, d, J=6.4 Hz), 4.11 (1H, t, J=6.4 Hz), 3.45 (3H, s).

2',7-Dibenzyloxy-4'-(methoxymethylenoxy)-isoflav-3-ene (G6). To a suspension of G5 (30.1 g, 58.5 mmol) in anhyd $CH_3CN$ (1 L), $PPh_3.HBr$ (20.1 g, 58.4 mmol) was added in five portions of ca. 4.0 g each at intervals of ca. 15-20 min. By the last addition, the reaction mixture became a clear solution. The progress of the reaction was checked by TLC ($CH_2Cl_2$: MeOH [15/1] as developing system). The reaction was complete in 1-2 h. Solvents were then evaporated to dryness under vacuum at rt to obtain an off-white residue which was used in the next step without further purification.

To a solution of product from the previous step in anhyd MeOH (1.5 L), potassium t-butoxide (13.1 g, 0.12 mol) was added with stirring. The reaction mixture was refluxed for 18-24 h. Reaction progress was monitored by TLC. After completion, the mixture was cooled to rt and filtered. The precipitate was dissolved in $CH_2Cl_2$. The organic layer was washed with $H_2O$ and dried over anhyd $Na_2SO_4$. After filtration, the solvents were evaporated under vacuum to obtain G6 (21.4 g, 44.5 mmol, 76% over two steps) as an off-white solid: mp 126-131° C. (Lit.[8] 115-118° C.); TLC $R_f$ 39 (hexanes: EtOAc [5:1]); 1H NMR (($CD_3)_2CO_3$ 600 MHz) δ 7.42 (10H, m), 7.28 (1H, d, J=8.4 Hz), 7.02 (1H, d, J=8.4 Hz), 6.81 (1H, d, J=2.4 Hz), 6.69 (1H, dd, J=2.4, 8.4 Hz), 6.61 (1H, s), 6.57 (1H, dd, J=2.4, 8.4 Hz), 6.47 (1H, d, J=2.4 Hz), 5.20 (2H, s), 5.13 (2H, s), 5.08 (2H, s), 4.91 (2H, s), 3.42 (3H, s); $^{13}C$ NMR (($CD_3)_2CO_3$ 150 MHz) δ 160.4, 159.2, 158.1, 155.6, 138.2, 137.7, 129.98, 129.91, 129.3, 129.2, 128.8, 128.7, 128.5, 128.34, 128.30, 122.5, 121.8, 118.0, 108.9, 102.9, 102.4, 95.0, 90:1, 71.0, 70.4, 68.9, 56.0.

2',7-Dibenzyloxy-4'-(t-butyldimethylsilyloxy)-isoflav-3-ene (G7). To a solution of 2',7-dibenzyloxy-4'-(methoxymethalenoxy)-isoflav-3-ene G6 (19.6 g, 40.8 mmol) in anhyd $CH_2Cl_2$ (200 mL) $PPh_3.HBr$ (17.6 g, 51.2 mmol) was added. The reaction mixture was stirred at rt for 1-2 h while followed by TLC (EtOAc/hexanes 1:2). After completion, $Et_3N$ (7.8 g, 75.6 mmol, 10 mL) and TBDMS-Cl (7.6 g, 50.4 mmol) were added. The reaction was stirred at rt for 12-15 h. After completion, solvents were evaporated under vacuum at 30° C. The solid residue was dissolved in $CH_2Cl_2$ (2 L) and oven-dried silica (340 g, dried overnight at 120° C. in oven and cooled in a desiccator) and a small amount of TFA were added and the mixture was gently stirred until complete disappearance of $PPh_3$ (TLC). After filteration, the filtrates were passed through a pad of silica. The solvents were evaporated under vacuum and the residue was recrystallized from $CH_2Cl_2$/MeOH (1:5) to obtain G7 (15.9 g, 28.6 mmol, 70%) as white crystals: mp 104-106° C. [lit.[8] 106-107° C.]; TLC $R_f$=0.42 [EtOAc/hexanes (1:2)]; $^1H$ NMR (($CD_3)_2CO_3$ 600 MHz) δ 7.40 (10H, m), 7.25 (1H, d, J=8.4 Hz), 7.02 (1H, d, J=8.4 Hz), 6.62 (2H, m), 6.57 (11H, dd, J=2.4, 8.4 Hz), 6.51 (1H, dd, J=2.4, 8.4 Hz), 6.47 (1H, d, J=2.4 Hz), 5.15 (2H, s), 5.10 (2H, s), 4.94 (2H, d, J=1.2 Hz), 0.97 (9H, s), 0.19 (6H, s); $^{13}C$ NMR (($CD_3)_2CO$, 150 MHz) δ 160.4, 158.1, 157.5, 155.6, 138.2, 137.9, 130.0, 129.8, 129.3, 129.2, 128.7, 128.57, 128.52, 128.3, 128.29, 128.28, 121.8, 118.1, 113.1, 108.9, 105.9, 102.9, 90.1, 70.9, 70.4, 68.9, 25.9, −4.3, −11.4; Anal. (%) calcd for $C_{17}H_{18}O_7$, C 76.30, H 6.95, found, C 76.02, H 7.09.

(+)-4'-t-Butyldimethylsilyloxy-2',7-(dibenzyloxy)isoflavan-3,4-diol (G8). To a solution of chiral ligand $(DHQD)_2$ PHAL (15.6 g, 20.0 mmol) in $CH_2Cl_2$ (80 mL), $OsO_4$ (5 g, 20.0 mmol) was added. After stirring at −20° C. for 1 h, a solution of G7 (10 g, 18.1 mmol) in $CH_2Cl_2$ (80 mL) was slowly added over 10-15 min and the mixture was stirred at −20° C. for 18-20 h. Reaction progress was monitored by TLC. After completion, the reaction was allowed to warm to rt, and 10% sodium sulfite (100 mL, ph~9.0) and 10% sodium bisulfite (100 mL, pH ~4) solution was added. After stirring at rt for 2 h, a mixture of THF/EtOAc (1:4, 1 L) was added to the reaction mixture and further stirred at 55° C. (external oil bath temp) for an additional 3-4 h. The reaction mixture was cooled to rt and filtered. The aq phase was extracted with EtOAc. The combined organic phase was washed with 0.1 M HCl, brine and dried over anhyd $Na_2SO_4$ and evaporated under vacuum. The product was recrystallized from EtOAc/hexanse to obtain G8 (10.2 g, 17.3 mmol, 95%, >98% ee) as a white solid: mp 75-77° C.; $[\alpha]^{25}_D$+6.7 (c 1.6, MeOH); TLC $R_f$=0.28 [EtOAc/hexanes (1:3)]; Chiral HPLC RT=10.35 min [Standard racemate RT=10.38 and 15.31 min], mobile phase was 2-propanol/hexanes (25:75) at 1.0 mL/min; $^1H$ NMR (($CD_3)_2CO$, 600 MHz) δ 7.59 (1H, dd, J=2.4. 8.4 Hz), 7.39 (11H, m), 6.58 (2H, m), 6.49 (1H, d, J=2.4 8.4 Hz), 6.38 (1H, d, J=2.4 Hz), 5.52 (1H, d, J=6.6 Hz), 5.20 (2H, s), 5.07 (2H, s), 4.73 (1H, d, J=11.4 Hz), 4.26 (1H, m), 4.21 (1H, m), 4.02 (1H, d, J=11.4 Hz), 0.96 (9H, s), 0.17 (6H, s); $^{13}C$ NMR (($CD_3)_2CO$, 100 MHz) δ 159.9, 157.4, 157.2, 155.7, 138.4, 137.8, 130.7, 130.1, 129.3, 129.2, 128.6, 128.6, 128.4, 128.2, 128.1, 123.5, 118.3, 112.4, 108.7, 106.1, 102.1, 72.0, 70.8, 70.2, 67.6, 25.9, 18.6, −4.3; Anal. (%) calcd for $C_{35}H_{40}O_6Si$, C 71.89, H 6.89, found, C 71.83, H 6.92.

(−)-9-(-t-Butyl dimethylsilyloxy)glycinol (G9). To a solution of G8 (5.01 g, 8.5 mmol) in anhydrous EtOH (110 mL) at 0° C., 10% Pd/C (1.01 g) was added. The mixture was stirred at rt for 4 h under hydrogen atmosphere (35 psi). Progress was followed by TLC. Prolonged reaction times can cause losses in overall yield. After completion, the reaction mixture was passed through a pad of Celite which was then washed with EtOH (3×50 mL). The combined solvents were evaporated under vacuum to obtain G9 (3.27 g, 8.5 mmol, 100%) as an off-white powder: mp 196-198 ° C.; $[\alpha]^{25}_D$−209.5 (c 0.3, MeOH); TLC $R_f$=0.41 [MeOH/$CH_2Cl_2$/hexanes (1:10:10)]; $^1H$ NMR (($CD_3)_2CO$, 600 MHz) δ 8.57 (1H, s), 7.31 (1H, d, I=8.4 Hz), 7.26 (1H, d, J=7.8 Hz), 6.56 (1H, dd, J=8.4 Hz, J=2.4 Hz), 6.46 (1H, dd, J=2.4, 8.4 Hz), 6.33 (1H, d, J=2.4 Hz), 6.27 1 H, d, J=1.8 Hz), 5.28 (1H, s), 5.03 (1H, s), 4.13 (1H, d, J=11.4 Hz), 4.01 (1H, d, J=11.4 Hz), 0.97 (9H, s), 0.20 (6H, s); $^{13}C$ NMR (($CD_3)_2CO$, 150 MHz) δ 161.6, 159.6, 158.6, 157.0, 133.1, 125.0, 123.6, 113.3, 113.0, 110.7, 103.7, 103.2, 90.1, 85.8, 76.6, 70.5, 25.9, −4.4, −11.4; Anal. (%) calcd for $C_{21}H_{26}O_5Si$, C 65.26, H 6.78, found, C 65.75, H 6.76.

Glycinol (GLO). To a solution of G9 (25 mg, 65 µmol) in ca. 1 mL of $CH_2Cl_2$ and MeOH (5:1), $Et_3N.3HF$ (33 µL, 195 µmol) buffered to pH 5-6 with excess of pyridine was added. The reaction mixture was allowed to stir for ca. 10 h at rt. The reaction was followed by TLC. After completion, the mixture was directly applied to CC [ca. 10 g silica gel; $CH_2Cl_2$:MeOH (10:1)]. The eluting solvents were evaporated under vacuum and the resulting yellowish solid was lyophilized to obtain GLO (14 mg, 51 µmol) as a yellow solid in ca. 78% yield: mp 108-112° C.; $[\alpha]^{25}_D$ –221.0 (c 0.3, MeOH); TLC $R_f$ 0.49 [hexanes:EtOAc (3:7)]; HREIMS m/z calcd for $C_{15}H_{12}O_5$ 272.0685, found 272.0678; chiral HPLC retention time (RT) 17.92 min [standard racemate RT 15.60 and 18.30 min]. Mobile phase was 2-propanol/hexane (15/85) at 1.5 mL/min; $^1H$ NMR[9] $((CD_3)_2CO$, 600 MHz) δ 8.55 (1H, s, Ar—OH), 8.47 (1H, s, Ar—OH), 7.30 (1H, d, J=9 Hz, H1), 7.20 (1H, d, J=7.8 Hz, H7), 6.55 (1H, dd, J=8.4 Hz, $^3J$=2.4 Hz, H2), 6.42 (1H, dd, J=8.4 Hz, $^3J$=2.4 Hz, H8), 6.31 (1H, d, $^3J$=2.4 Hz, H4), 6.24 (1H, d, $^3J$=2.4 Hz, H10), 5.26 (1H, s, H11a), 4.95 (1H, s, 6a-OH), 4.11(1H, d, J=11.4 Hz, H6'), 4.02 (1H, d, J=11.4 Hz, H6); $^{13}C$ NMR ($CD_3OD$, 150 MHz) δ 162.1, 161.1, 160.0, 157.3, 133.2, 125.1, 121.2, 113.0, 111.0, 109.2, 104.0, 98.9, 85.9, 77.2, 70.2; anal. (%) calc for $C_{15}H_{12}O_5.0.50H_2O.0.40CH_3OH$, C 62.90, H 5.00, found C 63.16, H 5.38.

Example 4

Preparation of Glyceollin I (G1) and Glyceollin II (G2) (Scheme 4)

9-(t-Butyldimethylsillyloxy)glyceollin I (G10) & II (G11). To a mixture of 6a-hydroxypterocarpan G9 (3.07 g, 7.94 mmol) in anhyd p-xylene (40 mL), 1,1-diethoxy-3-methyl-2-butene (2.6 g, 16.4 mmol, 3.1 mL) and 3-picoline (0.2 g, 2.1 mmol, 0.3 mL) were added successively under a flow of $N_2$. The reaction flask was fitted with a distillation assembly and was stirred at 125° C. (internal temp 120° C.). Progress of the reaction was followed by TLC. After completion, the reaction mixture was directly applied to a column and was purified by gravity column chromatography using a step gradient [first hexanes/$CH_2Cl_2$ (2:1), 450 mL then was changed to hexanes/$CH_2Cl_2$/EtOAc (20:10:1) to obtain G10 (2.2 g, 4.8 mmol, 60%) and G11 (0.22 g, 0.48 mmol, 10%), as off-white solid: (G10) mp 69-75 ° C.; TLC $R_f$ 0.57 [EtOAc/hexanes (1:2)]; $^1H$ NMR $((CD_3)_2CO$, 600 MHz) δ 7.28 (1H, d, J=8.4 Hz), 7.24 (1H, d, J=8.4 Hz), 6.57 (1H, d, J=10.2 Hz), 6.46 (2H, m), 6.28 (1H, d, J=2.4 Hz), 5.66 (1H, d, J=10.2 Hz), 5.28 (1H, s), 5.09 (1H, s,), 4.20 (1H, d, J=11.4 Hz), 4.08 (1H, d, J=11.4 Hz), 1.39 (3H, s), 1.35 (3H, s), 0.97 (9H, s), 0.20 (6H, s); Anal. (%) calcd for $C_{21}H_{26}O_5Si$, C 68.99, H 7.13, found, C 68.91, H 7.27; (G11) TLC $R_f$=0.44 [hexanes/EtOAc (1:1]; $^1H$ NMR ($CD_3COCD_3$, 600 MHz) δ 7.27 (1H, d, J=7.8 Hz), 7.15 (1H, s), 6.46 (1H, dd, J=1.8, 7.8 Hz), 6.41 (1H, d, J=9.6 Hz), 6.28 (1H, d, J=1.8 Hz), 6.22 (1H, s), 5.66 (1H, d, J=9.6 Hz), 5.26 (1H, s), 5.07 (1H, s), 4.15 (1H, d, J=11.4 Hz), 4.03(1H, d, J=11.4 Hz), 1.39 (3H, s), 1.36 (3H, s), 0.97 (9H, s), 0.20 (6H, s); $^{13}C$ $((CD_3)_2CO$, 150 MHz) δ 161.0, 158.0, 156.1, 154.6, 129.3, 129.1, 124.4, 121.5, 116.5, 113.5, 112.8, 104.8, 102.6, 100.3, 89.4, 85.0, 84.9, 76.5, 76.0, 69.9, 28.2 25.3, 25.2, 18.0, –5.0; Anal. (%) calcd for $C_{20}H_{18}O_5.0.75\ H_2O$, C 68.27, H 5.59, found C 68.36, H 5.59.

(–)-Glyceollin I (G1). To a solution of G10 (1 g, 2.2 mmol) in $CH_2Cl_2$ (30 mL), $Et_3N.3HF$ (30 mmol) and excess pyridine (45 mmol) were added. The reaction mixture was stirred at rt for 6 h. Progress was followed by TLC. After completion, solvents were evaporated under vacuum at 20° C. and directly applied to a flash column (silica ca. 20 g) using 'dry sample' loading techniques [EtOAc/hexanes (1:1)]. The eluting fractions were collected, solvents removed under vacuum, and the resulting residue was lyophilized after dissolving in a minimal amount of MeOH to obtain G1 (0.67 g, 1.97 mmol, 90%) as pinkish brown solid: mp 95-101° C.; $[\alpha]^{25}_D$ –202.6 (c 0.15, EtOAc); TLC $R_f$=0.33 (MeOH/$CH_2Cl_2$/hexanes (1:10:10)); Chiral HPLC RT=11.75 min [Standard racemate RT=11.74 and 13.51 min], mobile phase was 2-propanol/hexanes (10:90) at 1.5 mL/min; $^1H$ NMR ($CD_3OD$, 600 MHz) δ 7.21 (1H, d, J=8.4 Hz), 7.16 (1H, d, J=8.0 Hz), 6.60 (1H, d, J=10 Hz), 6.46 (1H, d, J=8.4 Hz), 6.40 (1H, dd, J=2.0, 8.4 Hz), 6.22 (1H, d, J=2 Hz), 5.62 (1H, d, J=10 Hz), 5.16 (1H, s), 4.16 (1H, d, J=11.6 Hz), 3.93 (1H, d, J=11.2 Hz), 1.38 (3H, s), 1.35 (3H, s); Anal. (%) calcd for $C_{20}H_{18}O_5.0.1H_2O$, C 70.62, H 5.39, found, C 70.35, H 5.65.

(–)-Glyceollin II (G2). (Obtained from scale-up synthesis of GLY I). To a solution of G11 (90 mg, 0.2 mmol) in $CH_2Cl_2$ (6 mL), $Et_3N.3HF$ (33 µL, 195 µmol) buffered to pH 5-6 with excess pyridine was added. The reaction mixture was stirred at rt for 6 h. The reaction was followed by TLC. After completion the mixture was concentrated to half of its original volume under vacuum at 20° C. and then was directly applied to the column for column chromatography (silica ca. 10 g, EtOAc/hexanes: (1:1)). The solvents were evaporated under vacuum to obtain G2 (50 mg, 0.15 mmol, 74%) as off white solid: mp 95-101° C.; TLC $R_f$:0.44 [EtOAc/hexanes (1:1)]; $^1H$ NMR ($CD_3OD$, 600 MHz) δ 7.15 (1H, d, J=8.4 Hz), 7.09 (1H, s), 6.39 (1H, dd, J=1.8, 8.4 Hz), 6.36 (1H, d, J=9.6 Hz), 6.23 (1H, s), 6.22 (1H, d, J=1.8 Hz), 5.60 (1H, d, J=10.2 Hz), 5.15 (1H, s), 4.10 (1H, dd, J=0.6, 11.4 Hz), 3.90 (1H, d, J=11.4 Hz), 1.38 (3H, s), 1.37 (3H, s); $^{13}C$ NMR ($CD_3OD$, 150 MHz) δ 162.1, 161.2, 157.1, 155.7, 130.3, 129.8, 125.1, 122.6, 121.1, 117.8, 114.3, 109.4, 105.2, 98.9, 85.7, 77.6, 77.1, 70.9, 28.3, 28.2; Anal. (%) calcd for $C_{20}H_{18}O_5.0.75H_2O$, C 68.27, H 5.59, found C 68.36, H 5.59.

Example 5

Preparation of Triphentriol (T5) (Scheme 5)

(4-Benzyloxy-2-hydroxy-phenyl)-(4-benzyloxy-phenyl)-methanone (T1). To a suspension of (2,4-dihydroxy-phenyl)-(4-hydroxy-phenyl)-methanone (9.2 g, 40 mmol) and oven dried potassium carbonate (11.6 g, 84 mmol) in acetone refluxing at 60° C., was added benzyl bromide (10 mL, 83 mmol) in two portions of 5 mL each, dropwise. The reaction was refluxed for 12 hours and solids were filtered and washed with 100 ml of $CH_2Cl_2$. The solvents combined and evaporated to give yellow product along with some tribenzylated side product, which was recrystallized from $CH_2Cl_2$:hexane (1:5) to get (9.84 g, 60%) of pure product T1. $^1H$ NMR (400 MHz, DMSO-d6) δ, 7.4 (m, 12H, Ar—H2'/6', $2×C_6H_5$), 6.97 (m, 3H, Ar—H3'/5', Ar—H6), 5.84 (d, 1H, Ar—H3), 5.6 (dd, 1H, Ar—H5), 5.14 (s, 2H, $PhCH_2$), 4.94 (s, 2H, $PhCH_2$).

5-Benzyloxy-2-[(4-benzyloxy-phenyl)-hydroxy-methyl]-phenol (T2). To a solution of (4-benzyloxy-2-hydroxy-phenyl)-(4-benzyloxy-phenyl)-methanone (T1) (1.6 g, 4 mmol) in 40 mL of THF:MeOH (1:1) was added sodium borohydride (0.160 g, 4 mmol) and solution stirred at 40° C. for 4 hours. After complete consumption of starting material (TLC) the solvents were evaporated, till about 5 mL remaining in the flask. The residue was carefully neutralized with 1 N $H_2SO_4$, till pH dropped to 6 and yellow solution turned colorless. This was extracted with 50 mL (4×EtOAc:water, 1:1). The organic layers were combined and dried over sodium sulfate and evaporated to give (1.12 g, 68%) of T2 as pinkish white solid. $^1H$ NMR (400 MHz, DMSO-d6) δ, 9.42(s, 1H, OH-Ph), 7.30(m, 13H, Ar—H2'/6', $2×C_6H_5$), 6.89 (d, 2H, Ar—H3'/5'), 6.44 (dd, 1H, $^2J$=8.4 Hz, $^3J$=2.4 Hz, Ar—H5), 6.38 (d, 1H, J=2.4 Hz, Ar—H3), 5.51 (d, 1H, CH—OH), 5.04 (s, 2H, PhCH$_2$), 4.99 (s, 2H, PhCH$_2$).

2-{5-Benzyloxy-2-[(4-benzyloxy-phenyl)-hydroxy-methyl]-phenoxy}-1-(4-benzyloxy-phenyl)-ethanone (T3). Potassium carbonate (0.165 g, 1.2 mmol) was added to a solution of 1-(4-benzyloxy-phenyl)-2-iodo-ethanone (P4) (0.352 g, 1 mmol) and 5-benzyloxy-2-[(4-benzyloxy-phenyl)-hydroxy-methyl]-phenol (P3) (0.412 g, 1 mmol) were in 40 mL of dry acetone and the mixture was refluxed for 6 hr. After completion of reaction (TLC), the solvent was evaporated and the residue extracted with EtOAc:water (3×40 mL). The organic layers were combined, dried over sodium sulfate and evaporated. The residue was dissolved in EtOAc and chromatographed over silica using hexanes: EtOAc (4:1) to give (0.381 g, 60%) yellowish solid product T3. $^1$H NMR (400 MHz, CDCl$_3$) δ, 7.88 (d, 2H , J=8.8 Hz, Ar—H2/6), 7.41-7.29 (m, 17H, 2×Ar—H, 3×C$_6$H$_5$), 7.07(d, 1H, J=8.8 Hz, 8.4 Hz), 7.02(d, 2H, J=8.8 Hz, Ar—H3/5), 6.92(d, 2H, J=8.8 Hz, 2×Ar—H), 6.54(dd, 1H, $^2J$=8.4 Hz, $^3J$=2.4 Hz, Ar—H4'), 6.5 (d, 1H, J=2.4 Hz, Ar—H6'), 6.04 (d, 1H, J=5.6 Hz, CH—OH), 5.24(m, 2H$_2$O—CH$_2$), 5.13 (s, 2H, PhCH$_2$), 5.04 (s, 2H, PhCH$_2$), 5.0 (s, 2H, PhCH$_2$).

7-Benzyloxy-3,4-bis-(4-benzyloxy-phenyl)-2H-chromene (T4). To a solution of 2-{5-Benzyloxy-2-[(4-benzyloxy-phenyl)-hydroxy-methyl]-phenoxy}-1-(4-benzyloxy-phenyl)-ethanone (T3) (0.636 g, 1 mmol) in 50 mL of CH$_3$CN was added triphenyl phosphine hydrobromide (0.377 g, 1.1 mmol) and the suspension was heated at 60° C. for about 2 hours. After disappearance of starting material (TLC), solvent was evaporated to give phosphonium salt. The solid was dissolved in 60 mL of anhydrous methanol followed by addition of potassium tert-butoxide (0.246 g, 2.2 mmol). The suspension was refluxed for 6 hours till completion of reaction (TLC). The solvent was evaporated and the residue extracted with EtOAc:H$_2$O (3×60 mL). The organic layers were combined, dried over sodium sulfate and evaporated. The residue was chromatographed over silica using hexanes:CH$_2$Cl$_2$ (4:1) to give (0.271 g, 45%) yellowish white solid product T4. $^1$H NMR (600 MHz, CDCl$_3$) δ, 7.44-7.31 (m, 15H, 3×C$_6$H$_5$), 7.04 (d, 2H, J=9 Hz, 2×Ar—H), 6.90 (m, 4H, 4×Ar—H), 6.77 (m, 3H, 3×Ar—H), 6.58 (d, 1H, J=2.4 Hz, 2×Ar—H), 6.47 (dd, 1H, $^2J$=8.4 Hz, $^3J$=2.4 Hz, Ar—H4'), 5.05 (s, 6H, PhCH$_2$), 4.98 (s, 2H, OCH$_2$).

3,4-Bis-(4-hydroxy-phenyl)-chroman-7-ol (T5). To a solution of 7-benzyloxy-3,4-bis-(4-benzyloxy-phenyl)-2H-chromene (T4) (0.061 g, 0.1 mmol) in THF was added 10% Pd—C (50 mg). This reaction mixture was hydrogenated at room temperature under 1 atm (15 psi) of H$_2$ pressure for ca. 4 hours. After the disappearance of starting material (TLC), the catalyst was filtered through a pad of celite. The celite-pad was washed with 10 mL of THF then 2×10 mL of methanol. The solution was filtered once more through filter paper and evaporated to obtain the brownish solid residue which was chromatographed over silica gel using CH$_2$Cl$_2$:EtOAc (3:1) to get (0.014 g, 42%) reddish white solid. $^1$H NMR (600 MHz, Acetone-d6) δ, 8.24 (s, 1H, OH), 8.17(s, 1H, OH), 8.09 (s, 1H, OH), 6.99-6.34 (m, 11H Ar—H), 4.34 (dd, 1H, O—CH), 4.11 (m, 3H, O—CH$_2$, 4-CH), 3.45 (m, 1H, 3-CH).

In accordance with the provisions of the patent statutes, the principle modes of operation of this invention have been explained and illustrated and the preferred embodiments have been disclosed. It is to be understood that this invention may be practiced otherwise than as specifically explained and illustrated without departing from its spirit or scope. In particular is a degree of flexibility within the synthetic methods to be used wherein different types of chemical protecting groups might also be deployed, providing that any of such other protecting groups also still meet the unique requirements disclosed within the general description of the broadest embodiments. For example, the inventors' specific description of the t-butyldimethylsilyl-group (TBDMS) as a distinct species, should be taken to include the use of the several other similar types of silyl-protecting groups, namely triethylsilyl (TES), triisopropyl (TIPS), or t-butyldiphenylsilyl (TBDPS). Likewise, the inventors' specific description of the benzyl-group and of the acetyl-group as distinct species, should be taken to include the use of other aryl or aralkyl ethers, and of other simple ester forming alkyl and aryl carboxylic acid groups.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

What is claimed is:

1. A process for preparing 4',7-dioxygenatedisoflav-3-ene compounds, comprising:

converting a compound of Formula I:

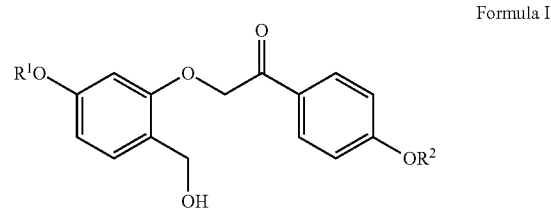

Formula I into a phosphonium salt intermediate of Formula II:

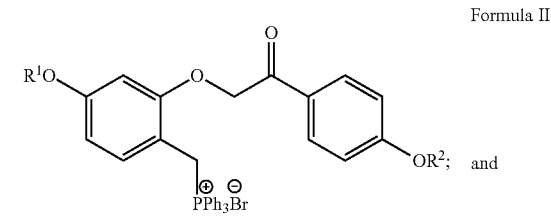

Formula II and accomplishing ring closure by an intramolecular Wittig reaction to produce a 4',7-dioxygenated-isoflav-3-ene compound of Formula III:

Formula III

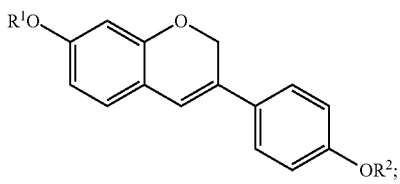

wherein $R^1$ and $R^2$ are either the same or independently H, alkyl, or a phenolic protecting group; and alkyl comprises a straight or branched alkane group having from 1 to 6 carbons.

2. The process of claim 1, wherein the phenolic protecting group comprises one or more of: benzyl, methoxymethyl (MOM), or a silyl derivative such as a tertiary-butyl-dimethylsilyl (TBDMS) group.

3. The process of claim 1, wherein converting a compound of Formula I into a phosphonium salt intermediate comprises treating a compound of Formula I with triphenylphosphine hydrobromide in distilled acetonitrile at ambient temperature, and accomplishing ring closure by an intramolecular Wittig reaction comprises placing the phosphonium salt intermediate in t-BuOK/methanol.

4. A composition comprising a compound made according to the process of claim 1, wherein the 4',7-dioxygenated-isoflav-3-ene compound is:

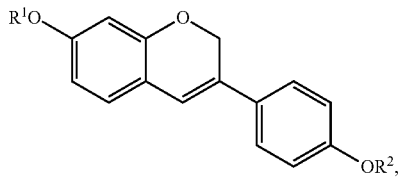

wherein $R^1 = R^2 = $ Bn; and a pharmaceutically acceptable salt thereof made from an acid or a base, or a stereoisomer thereof.

* * * * *

UNITED STATES PATENT AND TRADEMARK OFFICE
CERTIFICATE OF CORRECTION

PATENT NO. : 8,507,549 B2  
APPLICATION NO. : 13/346059  
DATED : August 13, 2013  
INVENTOR(S) : Paul W. Erhardt, Rahul S. Khupse and Amarjit Luniwal Page 1 of 1

It is certified that error appears in the above-identified patent and that said Letters Patent is hereby corrected as shown below:

In the Claims:

Column 20, Line 66, Claim 1, delete "isoflay" and insert -- isoflav --.

Signed and Sealed this  
Seventeenth Day of September, 2013

Teresa Stanek Rea  
*Deputy Director of the United States Patent and Trademark Office*